United States Patent [19]

Pasqualini et al.

[11] Patent Number: 5,399,339
[45] Date of Patent: Mar. 21, 1995

[54] PROCESS FOR THE PREPARATION OF NITRIDE COMPLEXES OF TRANSITION METALS

[75] Inventors: Roberto Pasqualini, Clamant; Véronique Comazzi, Issy-Les Moulineaux; Emmanuel Bellande, Champlan, all of France

[73] Assignee: CIS BIO International, Saclay, France

[21] Appl. No.: 965,250

[22] PCT Filed: Jul. 3, 1991

[86] PCT No.: PCT/FR91/00536
§ 371 Date: Jan. 21, 1993
§ 102(e) Date: Jan. 21, 1993

[87] PCT Pub. No.: WO92/00982
PCT Pub. Date: Jan. 23, 1992

[30] Foreign Application Priority Data

Jul. 4, 1990 [FR] France ............... 90 08473

[51] Int. Cl.$^6$ ............... C07F 13/00; C01B 21/06
[52] U.S. Cl. ............... 424/1.53; 534/10; 534/14; 556/45; 423/249; 423/409; 424/165
[58] Field of Search ............ 534/10, 14; 423/249, 423/409; 424/1.53, 1.65, 1.69; 556/45

[56] References Cited

U.S. PATENT DOCUMENTS

| | | | |
|---|---|---|---|
| 4,851,515 | 7/1989 | Bonnyman et al. | 534/14 |
| 5,279,811 | 1/1994 | Bergstein et al. | 534/10 X |
| 5,288,476 | 2/1994 | Pasqualini et al. | 534/10 X |
| 5,300,278 | 4/1994 | Pasqualini et al. | 534/14 |

FOREIGN PATENT DOCUMENTS

89/08657 9/1989 WIPO.

OTHER PUBLICATIONS

Kaden et al., *Isotopenpraxis*, "Nitridokomplexe des Technetium (V)", vol. 17 (1981) pp. 174–175.
Abram et al., *Inorg Chim Acta*, 109 (1985) "Lipophilic Technetium Complexes . . . " pp. L9–L11.
Abram et al., *J. Radioanal. Nuc. Chem.*, vol. 102, No. 2 (1986) "Lipophilic Techetium Complexes . . . " pp. 309–320.
International Journal of Radiation/Applications & Instrumentation Part A, vol. 39, No. 3, 1988, Pergamon Journals Ltd., (Marsh Barton, Exetor, GB); C. M. Kennedy et al: "A Formate Based Precursor for the Preparation of Technetium Complexes", pp. 213–225.

*Primary Examiner*—Robert L. Stoll
*Assistant Examiner*—Lara E. Chapman
*Attorney, Agent, or Firm*—Oblon, Spivak, McClelland, Maier & Neustadt

[57] ABSTRACT

Process for the preparation of nitride complexes of transition metals for use as radiopharmaceutical products or for the synthesis of novel pharmaceutical products. The process consists in reacting an oxygenic transition metal compound such as $99m_{Tc}$, $186_{Re}$ or $188_{Re}$, with a first nitrogenous ligand such as sodium nitride or a nitrogenous compound such as S-methyl, N-methyl dithiocarbazate, and a reducing agent consisting of either tin (II) or a dithionite. The product so obtained can be used for the preparation of radiopharmaceutical products by a reaction with a second ligand such as sodium dithiocarbamate.

23 Claims, No Drawings

PROCESS FOR THE PREPARATION OF NITRIDE COMPLEXES OF TRANSITION METALS

The present invention relates to a process for the preparation of transition metal complexes, more particularly usable as radiopharmaceutical products or for the synthesis of novel radiopharmaceutical products.

More specifically, it relates to the preparation of nitride complexes of transition metals having a part M≡N, in which M represents a transition metal.

It is pointed out that the term transition metal is understood to mean a metal, whose layer d is partly filled in the conventional degree of oxidation of said metal. These are metals of periods III to XII of the periodic table of elements with 18 columns. Examples of such metals are Tc, Ru, Co, Pt, Fe, Os, Ir, W, Re, Cr, Mo, Mn, Ni, Rh Pd, Nb and Ta.

The invention more particularly relates to the preparation of nitride complexes of radioactive transition metals usable as radiopharmaceutical products for diagnosis or therapy.

Among the complexes usable for diagnosis, particular reference is made to complexes of technetium 99 m. The complexes usable for therapy can e.g. be rhenium complexes.

Radiopharmaceutical products using the radionucleide $^{99m}Tc$ are compounds which are frequently used in nuclear medicine for diagnosis as a result of the physical and chemical characteristics of said radionuclide.

Thus, the latter only gives a gamma emission, has an optimum gamma energy for external detection (140 keV) and a short physical half-life (6.02 h), so that the patient is only given a low irradiation dose. Moreover, the cost of this radio-element is not very high and it is commercially available. Finally, the richness of technetium chemistry makes it possible to obtain a wide range of radiopharmaceutical products.

Thus, as stated by E. DEUTSCH et al in Progr. Inorg. Chem. (Australia), vol. 30, pp. 76–106, 1983, technetium can form very varied complexes with numerous ligands, at oxidation states ranging from VII to −I and coordination numbers between 4 and 9. Among the numerous complexes of said document, reference is made to complexes of $^{99m}Tc$ and $^{99}Tc$ in oxidation state V having a part Tc≡N.

Complexes of this type can be prepared by the process described by J. BALDAS et al in J. Chem. Soc. Dalton Trans., 1981, pp. 1798–1801; in Int. J. Appl. Radiat. Isot., 36, 1985, pp. 133–139 and in international patent application WO85/03063. This process firstly consists of preparing a compound of formula R+[$^{99m}Tc≡NX_4$], in which R+ is a cation such as sodium or ammonium and X represents a halogen atom such as Cl or Br and then reacting said compound with an appropriate ligand for obtaining the complex of $^{99m}Tc$ usable as a radiopharmaceutical product.

The complex R+[$^{99m}Tc≡NX_4$]− is of interest, because it is very stable to hydrolysis and can be used without modification of the component Tc≡N for substitution reactions with other ligands, which makes it possible to obtain a considerable diversity of technetium complexes.

The process known at present for the preparation of the intermediate compound R+[$^{99m}TCNX_4$]− consists of reacting a pertechnetate such as sodium pertechnetate with sodium nitride and a halogenated hydracid such as hydrochloric acid.

For carrying out this reaction, dry evaporation takes place of a sodium pertechnetate solution ($^{99m}Tc$) using a rotary evaporator, followed by the addition to the dry residue of sodium nitride and concentrated hydrochloric acid. Refluxing takes place for approximately 5 min in order to complete the reduction and destroy the nitride excess, followed by further dry evaporation using a rotary evaporator. This gives a residue containing the compound R+($^{99m}Tc≡NCl_4$)−.

It is difficult to apply this process to the manufacture of kits for medical use, because it takes a long time and has at least three stages in which a rotary evaporator is used twice, which is not easy in a nuclear medicine hospital department. Moreover, it is difficult to use this process for producing medical kits, because the sterility and apyrogeneity of solutions are difficult to control throughout the operations. Therefore, the product which is finally obtained must be sterilized prior to labelling by $^{99m}Tc$, either by passing over a sterilizing membrane, or by heat sterilization and it must undergo a pyrogen absence check before injecting into man.

In the case of the preparation of complexes usable for therapy, it is important to use a preparation process leading to a high yield of the desired products. However, in the case of the product developed by Baldas or Griffith (Coord. Chem. Rev., vol. 8, 1972, pp. 369–396) for the preparation of technetium nitride complexes, it is not possible to obtain high complex yields. The same is the case with the processes generally used for the preparation of rhenium-based pharmaceutical products.

International application WO 89/08657 describes a process for the preparation of nitride complexes of a transition metal, which obviates the disadvantages of the aforementioned process described by Baldas. This process consists of reacting an oxygen compound of a transition metal M with a first ligand chosen from within the group of substituted or non-substituted, aliphatic and aromatic phosphine and polyphosphine group and a second nitrogen ligand constituted either by a pharmaceutically acceptable metal or ammonium nitride, or by a nitrogen compound having a

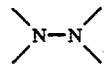

unit, in which the N's are connected to hydrogen atoms and/or monovalent organic groups by means of a carbon atom or in which one of the ends is connected to the carbon atom of a divalent organic group by means of a double bond and the other N is connected to hydrogen atoms and/or monovalent organic groups by means of a carbon atom.

According to this process, it is possible to easily obtain a nitride complex of a transition metal, because it is merely necessary to mix the above-described reagents in order to form the nitride complex. It is also possible to form other radiopharmaceutical products from said nitride complex by an exchange reaction with a third ligand.

Although this process is satisfactory and makes it possible to obtain numerous technetium nitride complexes, research has been continued with a view to further simplifying the preparation procedure for the technetium nitride complexes and for using reagents whose pharmacological and biological effects are well known in order to limit the preliminary studies required with a view to the marketing of the novel radiopharmaceutical products.

The present invention relates to a process for the preparation of nitride complexes of transition metals, based on the use of known reducing agents, which are often used for the preparation of technetium complexes other than nitride complexes.

According to the invention, the process for the preparation of a product incorporating a nitride complex of a transition metal having a part $M\equiv N$, with M representing a transition metal, consists of reacting in solution an oxygen compound of the transition metal M with:

1°) a first nitrogen ligand constituted either by a pharmaceutically acceptable metal or ammonium nitride, or by a nitrogen compound having a

unit, in which the N's are connected to hydrogen atoms and/or monovalent organic groups, e.g. by means of a carbon atom or a S atom, or in which one of the N's is connected to the carbon atom of a divalent organic group by a double bond and the other N is connected to hydrogen atoms and/or to monovalent organic groups, e.g. by a carbon atom and 2°) a reducing agent constituted either by a pharmaceutically acceptable metal or ammonium dithionite, or by tin (II) present in ionic form in the solution.

Thus, in this process, the polyphosphines or phosphines of international application WO 89/08657 are replaced either by tin (II), or a pharmaceutically acceptable metal or ammonium dithionite.

This considerably modifies the development of novel radiopharmaceutical products such as technetium-based products, because the toxicity and biological effects of tin, which can be used in the form of a tin salt, such as tin chloride, are well known, which is not the case with the phosphines and polyphosphines of international application WO 89/08657.

Thus, tin has long been used for the preparation of technetium complexes of the pyrophosphate, methylene diphosphonate and hydroxymethylene diphosphonate types.

Moreover, the tin (II) compounds and dithionites are generally soluble in water, which simplifies the preparation of the transition metal nitride complex, because it is possible to work in an aqueous solution, i.e. in an appropriate medium for administration to man and living beings. Morover, these compounds are stable and do not react with substrates such as fragments F(ab')$_2$ of antibodies.

In addition, according to a variant of the process according to the invention, use is also made of a second organic ligand, an antibody, an antibody fragment, a protein or a peptide, which makes it possible to give the end product the sought biological properties and in particular the desired tropism.

In this case, reaction takes place in solution of an oxygen compound of the transition metal M with:

1°) a first nitrogen ligand constituted either by a pharmaceutically acceptable metal or ammonium nitride, or by a nitrogen compound having a

unit, in which the N's are connected to hydrogen atoms and/or to monovalent organic groups, e.g. by means of a carbon atom or a S atom, or in which one of the N's is connected to the carbon atom of a divalent organic group by means of a double bond and the other N is connected to hydrogen atoms and/or to monovalent organic groups, e.g. by means of a carbon atom;

2°) a reducing agent constituted either by a pharmaceutically acceptable metal or ammonium dithionite, or by tin (II) present in ionic form in the solution; and 3°) a second organic ligand with nucleophilic groups, a monoclonal antibody, an antibody fragment, a protein or a peptide.

On using said second organic ligand, said antibody, said protein or said peptide, there is probably an exchange reaction between the first nitrogen ligand which is contributed to the preparation of the part $M\equiv N$ and the second organic ligand, the antibody, the protein or the peptide.

These two reactions can be performed simultaneously by reacting all the reagents at the same time in the solution. However, it is generally preferable to work in two stages. Thus, in a first stage the oxygen compound of the transition metal is reacted with the first ligand and the reducing agent, and in a second stage the product obtained at the end of the first stage is reacted with the third ligand, monoclonal antibody, antibody fragment, protein or peptide.

The process according to the invention can be performed in different ways, which more particularly depend on the reducing agent used and the choice of the first and second ligands.

According to a first embodiment of the invention, the reducing agent used is tin (II) and it is introduced into the solution from one or more reagents able to maintain it in ionic form in the presence of the first and possibly the second ligand in order to avoid the precipitation of the tin complexes liable to form with the first or second ligand.

Thus, it is possible to introduce the tin in the form of tin (II) salt, when the anion of said tin salt has a better complexing power on tin than the other reagents present in the solution, i.e. the first nitrogen ligand and optionally the second ligand. For example, the tin salt can be tin oxalate or tartrate.

It is also possible to introduce the tin (II) and maintain it in ionic form in the solution from other tin salts such as tin sulphate and halides and in particular tin chloride, provided that there is a simultaneous addition to the solution of a complexing agent having a complexing power with respect to tin which is stronger than those of the nitrogen ligand and the second, optionally used ligand. In this case tin (II) chloride and an appropriate complexing agent are added to the solution of the transition metal oxygen compound and the first nitrogen ligand.

As examples of usable complexing agents, reference is made to ammonium or alkali metal pyrophosphates, ammonium or alkali metal glucoheptonates, ammonium or alkali metal diethylene triaminopentaacetates, ammonium or alkali metal ethylene diaminotetraacetates, ammonium or alkali metal 1,2-diaminopropane-N,N,N',N'-tetraacetates, ammonium or alkali metal gluconates, ammonium or alkali metal methylenediphosphonates, ammonium or alkali metal hydroxymethylene diphosphonates and ammonium or alkali metal citrates.

In general terms, it is possible to use as the complexing agent all tin complexing agents such as phosphonates, polyphosphates and polyaminocarboxylic acids.

According to a second embodiment of the process according to the invention, the reducing agent is a pharmaceutically acceptable metal or ammonium dithionite. Pharmaceutically acceptable metal dithionites can in particular be alkali metal dithionites, e.g. sodium dithionite.

As has been seen hereinbefore, according to the invention, preferably the reaction between the oxygen compound of the transition metal, the nitrogen ligand and the reducing agent takes place in an aqueous solution, whose pH is adjusted to an appropriate value. However, it is also possible to work in alcoholic or hydroalcoholic solutions.

It is possible to work within a wide pH range, e.g. between 1.5 and 11, but preferably at a pH between 7.4 and 8.

In order to carry out the reaction, it is possible to aseptically introduce a sterile solution of the transition metal oxygen compound and add to it a sterile solution of the nitrogen ligand and the reducing agent, whose pH has been adjusted to the desired value by the addition of acid, base or an appropriate buffer. It is then possible to carry out the reaction at ambient temperature or at a higher temperature e.g. between 50° and 100° C. for variable times, which are in particular dependent on the temperature used.

In general, working takes place with molar ratios of the transition metal oxygen compound to the first nitrogen ligand of $10^{-9}$ to $10^{-2}$.

The quantities of the first nitrogen ligand and the reducing agent used can be very low and vary within a wide range between e.g. 0.03 and 30 μmole/ml for the first nitrogen ligand and 0.02 and 2 μmole/ml for the reducing agent.

Following said reaction, it is possible to add the second ligand, the monoclonal antibody, the antibody fragment, the protein or the peptide and allow it to react at ambient temperature or a higher temperature which can e.g. extend up to 37° to 45° C. for antibodies or 100° C. for molecules resisting said temperature, for variable times, which more particularly depend on the temperature used.

In general, working takes place with molar ratios between the transition metal oxygen compound and the second ligand of $10^{-9}$ and $10^{-2}$. In the case where use is made of an antibody, the molar ratio between the transition metal oxygen compound and the antibody is $10^{-3}$ to $10^{-1}$.

In said second stage, it is also possible to adjust the pH of the solution to an appropriate value by introducing the second ligand into an aqueous solution having a suitable pH. The pH used can vary within a wide range, e.g. 3.5 to 11 and preferably working takes place at a physiological pH.

It is also possible to carry out said second stage in the presence of other additives, e.g. a complexing agent making it possible to avoid the reaction of the tin with the second ligand used, more particularly for avoiding the formation of precipitates.

As previously, this second reaction is preferably performed in an aqueous solution, but it would also be possible to perform it in an alcoholic or hydroalcoholic solution, or carry out the first and second stages in different solutions, e.g. the first stage in an aqueous solution and the second stage in an alcoholic or hydroalcoholic solution or vice versa.

For performing the second stage, it is possible to use various organic ligands, because their choice is only dependent on the properties which it is wished to give to the final complex.

Thus, it is possible to use as the second ligand amines, thiols, thioethers, oximes, phosphines and polyfunctional ligands of the polyaminopolythiol type.

For example, it is in particular possible to use compounds complying with the formula:

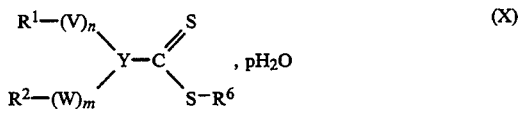

in which V and W, which can be the same or different, represent O, S or Se, n and m, which can be the same or different, are equal to 0 or 1, Y represents N, P or As and $R^1$ and $R^2$, which can be the same or different, represent a straight or branched alkyl radical with 1 to 10 carbon atoms, substituted or not by —O—$R^3$, OO-C—$R^3$, OCNR$^4$R$^5$ or —NR$^4$R$^5$ groups, in which $R^3$ is a straight or branched alkyl radical with 1 to 5 carbon atoms and $R^4$ and $R^5$, which can be the same or different, are hydrogen atoms or straight or branched alkyl radicals with 1 to 5 carbon atoms, or in which $R^1$ and $R^2$ together form a hydrocarbon carbon cycle optionally containing one or more heteroatoms, and $R^6$ is an alkali metal ion, H$^+$ or NH$_4^+$, and p=0 is an integer from 1 to 5.

Ligands of this type are more particularly described in international application WO/90 06137 for producing radiopharmaceutical products having in particular a cardiac tropism. Examples of such ligands are sodium diethyl dithiocarbamate.

Examples of second ligands usable in the process according to the invention are thioquinoline, penicillamine, sodium ethyl dithiocarboxylate, sodium isopropylxanthate and sodium diethyl dithiophosphinate.

In said second stage, it is also possible to use a monoclonal antibody or an antibody fragment.

When the reaction is performed with a monoclonal antibody or an antibody fragment, it is possible in this way to prepare an antibody labelled by a transition metal. For this reaction, the monoclonal antibody or antibody fragment used can be activated, e.g. by pretreatment with aminoethane thiol or dithiothreitol, in order to convert the disulphide bonds into a sulphydryl group.

It is possible to use numerous antibody types and in particular those able to combine with the M=N part by means of sulphur atoms. Examples of such antibodies are anti-ACE (anti-carcinoembryonic antigen), antibodies, anti-ovarian carcinoma antibodies, (OC125), anticolorectal antibodies, antifibrin and anti-myosin.

The labelled antibody fragment or antibody obtained is very interesting, e.g. for detecting tumours. Thus, following the reaction with the transition metal complex, the monoclonal antibody or antibody fragment is linked with the transition element such as technetium⁹⁹ᵐ, but it can react with the corresponding antigens. Thus, the specificity of the antibody is maintained and the labelled antibody is stable. It is also possible to use said labelled antibody for detecting tumours, because it will be naturally directed towards the corresponding antigen and will make it visible to render possible the tumours.

In the second stage, it is also possible to use a protein or a peptide with a view to giving the desired tropism to the radiopharmaceutical product obtained.

According to the invention, the first nitrogen ligand used making it possible to form the transition metal nitride complex can be of different types. Thus, it is possible to use either an alkali metal or ammonium nitride, or a nitrogen compound. The nitrogen compounds can comply with the formula:

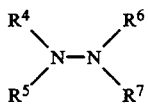

in which $R^4$, $R^5$, $R^6$ and $R^7$, which can be the same or different, represent a hydrogen atom, an alkyl radical, an aryl radical, an alkoxy radical, an alkyl radical substituted by at least one group chosen from among hydroxy, carboxy, amino, amido and mercapto radicals, an aryl radical substituted by at least one group chosen from among halogen atoms and alkoxy, hydroxy, amino and mercapto radicals and amino radicals substituted by at least one alkyl radical, a radical complying with the formulas:

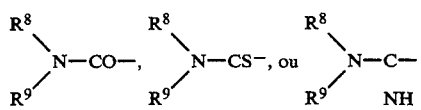

in which $R^8$ and $R^9$, which can be the same or different, represent a hydrogen atom, an alkyl radical, or an amino radical, a radical of formula:

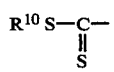

in which $R^{10}$ represents a hydrogen atom, an alkyl radical or an aryl radical, a radical of formula $R^{11}$—CO— with $R^{11}$ representing an alkyl radical, an alkoxy radical, an aryl radical which is not substituted or substituted by at least one group chosen from among halogen atoms and hydroxy radicals, or a radical derived from a heterocycle which is not substituted or substituted by at least one group chosen from among halogen atoms and hydroxy radicals or a radical derived from a heterocycle which is not substituted or substituted by at least one group chosen from among halogen atoms and hydroxy radicals, or in which $R^4$ and $R^5$ can together form a divalent radical of formula:

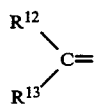

in which $R^{12}$ represents —CH₂—NH₂—, an aryl radical which is not substituted or substituted by at least one group chosen from among halogen atoms and hydroxy, alkoxy, amino and mercapto radicals and amino radicals substituted by at least one alkyl radical, or a radical derived from a heterocycle which is not substituted or substituted by one or more groups chosen from among halogen atoms and hydroxy, alkoxy, amino and mercapto radicals and amino radicals substituted by at least one alkyl radical and $R^{13}$ represents a hydrogen atom, an alkyl radical or an alkyl radical substituted by at least one group chosen from among hydroxy, carboxy, amino, amido and mercapto radicals, and $R^6$ and $R^7$ have the meanings given hereinbefore.

Examples of such nitrogen compounds are described in detail in international application WO 89/08657.

It is also possible to use as the first nitrogen ligand in the invention, ligands complying with the formula:

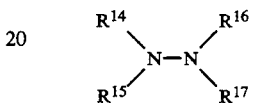

in which $R^{14}$, $R^{15}$ and $R^{16}$, which can be the same or different, represent a hydrogen atom, an alkyl radical, an aryl radical, an alkoxy radical, an alkyl radical substituted by at least one group chosen from among hydroxy, carboxy, amino, amido and mercapto radicals, or an aryl radical substituted by at least one group chosen from among halogen atoms and alkoxy, hydroxy, amino and mercapto radicals and amino radicals substituted by at least one alkyl radical, $R^{17}$ represents a radical complying with the formulas

or

in which $R^{18}$ is a phenyl group, which is not substituted or substituted by at least one substituent chosen from among halogen atoms and alkyl radicals and $R^{19}$ is a hydrogen atom, —NH₂ or a radical chosen from among alkyl radicals, alkyl radicals substituted by at least one group chosen from among cyano, pyridyl and —CO—NH—NH₂ groups, the phenyl radical, the phenyl radical substituted by at least one substituent chosen from among —OH, NH₂ and the alkyl and alkoxy radicals.

In this formula, the alkyl and alkoxy radicals can be straight or branched radicals, preferably having 1 to 4 carbon atoms, e.g. the methyl or methoxy radical.

The aryl radicals are radicals derived from a necleus by the elimination of a hydrogen atom, e.g. the phenyl and naphthyl radicals.

The use of such ligands is of interest, because it makes it possible to carry out the first reaction at ambient temperature for the formation of the intermediate and then prepare a radiopharmaceutical product having a radiochemical purity of at least 95%, by reacting said intermediate with a second ligand.

Preferably, when it is wished to carry out the reaction at ambient temperature, the first nitrogen ligand complies with the aforementioned formula:

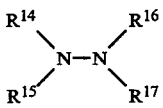

in which $R^{14}$, $R^{15}$ and $R^{16}$ are hydrogen atoms, $R^{17}$ represents the radical of formula $SO_2R^{18}$ with $R^{18}$ having the meaning given hereinbefore, or the radical of formula:

The nitrogen ligands complying with the above formulas can also be used at ambient temperature whilst bringing about the same advantages as in the process described in WO 89/08657. In this case, the intermediate is formed by the reaction of an oxygen compound of the transition metal with a ligand chosen from within the group of substituted or unsubstituted, aliphatic and aromatic phosphines and polyphosphines, and the nitrogen ligand of formula:

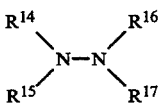

described hereinbefore.

According to the invention, the transition metal oxygen compound is advantageously an ammonium or alkali metal 99 m pertechnetete or an ammonium or alkali metal 188 or 186 perrhenate.

The invention also relates to a kit for the preparation of a radiopharmaceutical product comprising a transition metal nitride complex. This kit contains a first bottle containing the first nitrogen ligand and the reducing agent, as well as a second bottle containing a second organic ligand with a nucleophilic group, a monoclonal antibody, an antibody fragment, a protein or a peptide.

Thus, with said kit, it is possible to directly prepare the desired radiopharmaceutical product in a nuclear medicine hospital department by mixing the content of the two bottles and adding to them e.g. an ammonium or alkali metal pertechnetate solution.

The first ligand, the reducing agent and the second ligand can be respectively present in bottles in liquid or lyophilized form.

Other features and advantages of the invention can be gathered from reading the following, non-limitative, illustrative examples.

EXAMPLE 1

Preparation Of A $^{99m}Tc$ Nitride Complex.

This example uses as the reducing agent tin II introduced from tin chloride and a complexing agent constituted by sodium pyrophosphate, in order to maintain the tin in ionic form in the solution. The reaction is performed in aqueous solution and the pH is adjusted to a value of 7 by adding a phosphate buffer.

Into a penicillin-type bottle are introduced 0.5 to 3 ml of a sterile sodium pertechnetate (technetium-99 m) solution corresponding to a radioactivity from 18 MBq to 18.5 GBq (0.5 to 500 mCi), 1 ml of a phosphate buffer having a molar concentration from 0.1 to 0.5M and a pH of 7.4 to 8, 0.1 to 0.5 ml of an aqueous solution containing $2 \cdot 10^{-2}$ mole/1 (2.7 mg/ml) of S-methyl, N-methyl dithiocarbazate and 0.1 to 0.3 ml of an aqueous solution containing $1.8 \cdot 10^{-3}$ mole/1 of dihydrated tin (II) chloride and $5.6 \cdot 10^{-2}$ mole/1 of sodium pyrophosphate.

The reaction is performed at ambient temperature for 30 min giving a product containing a nitride complex of technetium-99 m.

EXAMPLES 2 to 13

The same operating procedure as in example 1 is followed for the preparation of products containing a technetium nitride complex using the same nitrogen ligand, the same technetium oxygen compound and as the reducing agent tin chloride with a complexing agent. In all cases it is $SnCl_2$, $2H_2O$. The reagents used, their quantities and the reaction conditions are given in table 1.

In example 10, where sodium gluconate is used as the complexing agent, it is not necessary to add phosphate buffer for adjusting the pH.

The products obtained in these examples are intermediates containing a technetium 99 m complex, which could then be used for the preparation of radiopharmaceutical products based on $^{99m}Tc$.

EXAMPLES 14 TO 17

In these examples use is made of the same operating procedure as in example 1 and the same transition metal oxygen compound and the same nitrogen ligand are used, as well as a phosphate buffer, but in this case the reducing agent is constituted by a tin salt, which remains in the ionic stage in the aqueous solution without an addition of a complexing agent. The reagents and reaction conditions used in these examples are given in table 1.

EXAMPLES 18 TO 23

In these examples the same operating procedure as in example 1 is used, but different nitrogen ligands are used and optionally additives other than the phosphate buffer, with the same technetium oxygen compound and a reducing agent constituted by tin chloride $SnCl_2$, $2H_2O$ associated with sodium pyrophosphate. The reagents used, their quantity and the reaction conditions are given in table 1. Table 1 shows that the nature of the added additive for the adjustment of the pH is more particularly dependent on the nitrogen ligand used.

EXAMPLE 24

In this example use is made of the same operating procedure as in example 1, but the reducing agent is constituted by 0.2 ml of a solution containing $6 \cdot 10^{-2}$ mole/l of sodium dithionite in water. The reaction conditions and reagent quantities used are given in table 1.

EXAMPLES 25 TO 46

In these examples use is made of products prepared in examples 1 to 24 for the formation in a second stage of nitride complexes of technetium-99m with sodium diethyldithiocarbamate, which leads to radiopharmaceutical products having in particular a cardiac tropism.

When the reducing agent used in the first stage is tin, it is preferable to carry out the second stage in the presence of a complexing agent having a complexing power with respect to tin higher than that of dithiocarbamate, because if not there would be a tin dithiocarbamate precipitation. In addition, although said precipitate does not deteriorate the radiochemical purity of the nitride complex of $^{99m}$Tc addition takes place of 0.2 ml of a solution of a complexing agent constituted by 1,2 N,N,N′,N′-diaminopropane tetraacetic acid in solution in water at a concentration of 50 mg/ml. This acid can replace the tin complexing agents used in the first stage such as pyrophosphate, gluconate, etc.

The following procedure is used in example 25. To the bottle containing the product prepared in example 1 are added 0.2 ml of a solution containing 0.33 mole/l of 1,2N,N,N′,N′-diaminopropane tetraacetic acid in water and then 0.5 ml of a solution containing $4 \cdot 10^{-2}$ mole/l of sodium diethyldithiocarbamate in water, at a pH of 7.5 to 11. The reaction is carried out for 15 min at 100° C.

The radiochemical purity of the complex obtained is tested by thin layer chromatography (TLC) using a silica gel and a mixture of dichloromethane and toluene in a volume ratio of 1:1 as the solvent. The complex obtained has a Rf of 0.4 to 0.5. The radiochemical purity is better than 93%.

A comparison with a sample of nitride-bis (diethyldithiocarbamate)$^{99}$Tc obtained in accordance with the Baldas method described in J. Chem. Soc. Dalton Trans. 1981, pp. 1798–1801 shows that it is indeed the same technetium nitride complex.

In examples 26 to 46 the same operating procedure as in example 25 is used, using products other than that described in example 1 and optionally different reaction conditions. The reaction conditions, the reagents used and their quantities are given in table 2. This table also shows the radiochemical purity of the complex obtained. This table makes it clear that the process according to the invention makes it easily possible to obtain nitridebis(diethyldithiocarbamate)$^{99m}$Tc with a high degree of radiochemical purity.

In example 31, it is not necessary to add a complexing agent, because the product prepared in example 8 contains 1,2 N,N,N′,N′-diaminopropane tetraacetic acid.

EXAMPLE 46

In this example, preparation directly takes place of a radiopharmaceutical product by simultaneously mixing the nitrogen ligand, the reducing agent and the second ligand.

This follows the same operating procedure as in example 1 and the same reagent quantitities are used, but introduction also takes place into the bottle of 0.5 ml of a $4 \cdot 10^{-2}$ mole/l diethyldithiocarbamate solution. The pH is between 7.5 and 8.5 and the reaction is allowed to continue for 30 minutes at 100° C. The radiochemical purity of the complex obtained is 92%.

EXAMPLES 47 to 69

The same operating procedure as in example 1 is followed for preparing products containing a technetium nitride complex using as the first nitrogen ligand the ligands referred to in table 3, as the reducing agent SnCl$_2$, 2H$_2$O with a complexing agent constituted by 1,2 N,N,N′N′-diaminopropane tetraacetic acid and as the technetium oxygen compound s sterile sodium pertechnetate solution (Tc-99m) corresponding to a radioactivity between 18MBq and 18.5 GBq (0.5 to 500 mCi).

The reagents used, their quantities and the reaction conditions are given in table 3. This table makes it clear that it is possible to carry out the reaction at ambient temperature with numerous nitrogen ligands. The products obtained in these examples are intermediates containing a technetium 99m complex and which could then be used for the preparation of radiopharmaceutical products based on $^{99m}$Tc.

EXAMPLES 70 to 97

In these examples use is made of the products prepared in examples 47 to 69 and the product prepared in example 8 for forming in a second stage technetium-99m nitride complexes with a second ligand constituted by sodium diethyldithiocarbamate and by the different ligands given in table 4. Thus, radiopharmaceutical products are obtained.

In these examples, the operating procedure of example 31 is followed using the reagents and reaction conditions given in table 4. Table 4 also indicates the radiochemical purity of the complex obtained, which was determined by thin layer chromatography as in example 25.

The table makes it clear that the process according to the invention permits the obtaining in easy manner of various technetium nitride complexes usable as radiopharmaceutical products and with a high degree of radiochemical purity, even when working at ambient temperature. It is also possible to operate at a physiological pH, which is advantageous for use in diagnosis and therapy.

Therefore the process according to the invention is of great interest, because it permits working under gentle conditions (ambient temperature and/or physiological pH) when the appropriate ligands are chosen.

TABLE 1

| Ex. | 1st nitrogen ligand | Reducing agent | Other additive | M oxygen compound | Reaction conditions |
|---|---|---|---|---|---|
| 1 | (0.1–0.5 ml) S-methyl, N-methyl dithiocarbazate ($2 \cdot 10^{-2}$ mole/l 2.7 mg/ml) | (0.1–0.3 ml) SnCl$_2$, 2H$_2$O ($1.8 \cdot 10^{-3}$ mole/l) sodium pyrophosphate ($5.6 \cdot 10^{-2}$ mole/l) | (1 ml) phosphate buffer (0.1–0 5 mole/l) (pH: 7.4–8) | (0.5–3 ml) Na pertechnetate ($^{99m}$Tc) 18 MBq to 3.7 GBq (0.5–100 mCi) | ambient temperature, 30 min |
| 2 | (0.1–0.5 ml) S-methyl, N-methyl dithiocarbazate ($2 \cdot 10^{-2}$ mole/l 2.7 mg/ml) | (0.1–0.3 ml) SnCl$_2$, 2H$_2$O ($1.8 \cdot 10^{-3}$ mole/l) sodium pyrophosphate ($5.6 \cdot 10^{-2}$ mole/l) | (1 ml) phosphate buffer (0.1–0 5 mole/l) (pH: 7.4–8) | (0.5–3 ml) Na pertechnetate ($^{99m}$Tc) 18 MBq to 3.7 GBq (0.5–100 mCi) | 100° C., 20 min |
| 3 | (0.1–0.5 ml) S-methyl, N-methyl dithiocarbazate ($2 \cdot 10^{-2}$ mole/l 2.7 mg/ml) | (0.1–0.3 ml) SnCl$_2$, 2H$_2$O ($1.8 \cdot 10^{-3}$ mole/l) sodium pyrophosphate ($5.6 \cdot 10^{-2}$ mole/l) | (1 ml) phosphate buffer (0.1–0 5 mole/l) (pH: 7.4–8) | (0.5–3 ml) Na pertechnetate ($^{99m}$Tc) 18 MBq to 3.7 GBq (0.5–100 mCi) | 100° C., 30 min |
| 4 | (0.1–0.5 ml) S-methyl, N-methyl | (0.1–0.3 ml) SnCl$_2$ ($1.8 \cdot 10^{-3}$ | (1 ml) phosphate buffer | (0.5–3 ml) Na pertechnetate | 100° C., 30 min |

TABLE 1-continued

| Ex. | 1st nitrogen ligand | Reducing agent | Other additive | M oxygen compound | Reaction conditions |
|---|---|---|---|---|---|
| | dithiocarbazate<br>($2 \cdot 10^{-2}$ mole/l<br>2.7 mg/ml | mol/l sodium glucoheptonate<br>(0.18 mole/l) | (0.1–0 5 mole/l<br>(pH: 7.4–8) | ($^{99m}$Tc)<br>18 MBq to 3.7 GBq<br>(0.5–100 mCi) | |
| 5 | (0.1–0.5 ml)<br>S-methyl, N-methyl<br>dithiocarbazate<br>($2 \cdot 10^{-2}$ mole/l<br>2.7 mg/ml | (0.1–0.3 ml)<br>SnCl$_2$ ($5 \cdot 10^{-4}$<br>mole/l sodium diethylene<br>triamino pentaacetate<br>(DTPA)<br>($6 \cdot 10^{-3}$ mole/l | (1 ml)<br>phosphate buffer<br>(0.1–0 5 mole/l<br>(pH: 7.4–8) | (0.5–3 ml)<br>Na pertechnetate<br>($^{99m}$Tc)<br>18 MBq to 3.7 GBq<br>(0.5–100 mCi) | Ambient temperature<br>30 min |
| 6 | (0.1–0.5 ml)<br>S-methyl, N-methyl<br>dithiocarbazate<br>($2 \cdot 10^{-2}$ mole/l<br>2.7 mg/ml | (0.1–0.3 ml)<br>SnCl$_2$ ($5 \cdot 10^{-4}$<br>mole/l sodium diethylene<br>triamino pentaacetate<br>(DTPA)<br>($6 \cdot 10^{-3}$ mole/l | (1 ml)<br>phosphate buffer<br>(0.1–0 5 mole/l<br>(pH: 7.4–8) | (0.5–3 ml)<br>Na pertechnetate<br>($^{99m}$Tc)<br>18 MBq to 3.7 GBq<br>(0.5–100 mCi) | 100° C., 30 min |
| 7 | (0.1–0.5 ml)<br>S-methyl, N-methyl<br>dithiocarbazate<br>($2 \cdot 10^{-2}$ mole/l<br>2.7 mg/ml | (0.1–0.3 ml)<br>SnCl$_2$ ($5 \cdot 10^{-4}$<br>mole/l sodium ethylene<br>diamino tetraacetate<br>(EDTA)<br>($6 \cdot 10^{-3}$ mole/l | (1 ml)<br>phosphate buffer<br>(0.1–0 5 mole/l<br>(pH: 7.4–8) | (0.5–3 ml)<br>Na pertechnetate<br>($^{99m}$Tc)<br>18 MBq to 3.7 GBq<br>(0.5–100 mCi) | 100° C., 30 min |
| 8 | (0.1–0.5 ml)<br>S-methyl, N-methyl<br>dithiocarbazate<br>($2 \cdot 10^{-2}$ mole/l<br>2.7 mg/ml | (0.2–0 5 ml)<br>SnCl$_2$ ($4 \cdot 10^{-3}$<br>mole/l Na diamino-<br>1,2-propane-N,N,N',N'-<br>tetraacetate<br>(0.16 mole/l) | (1 ml)<br>phosphate buffer<br>(0.1–0 5 mole/l<br>(pH: 7.4–8) | (0.5–3 ml)<br>Na pertechnetate<br>($^{99m}$Tc)<br>18 MBq to 3.7 GBq<br>(0.5–100 mCi) | 100° C., 30 min |
| 9 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>SnCl$_2$ ($3 \cdot 10^{-4}$<br>mole/l Na glucoheptonate<br>(0.18 mole/l) | (1 ml)<br>phosphate buffer<br>(0.1–0 5 mole/l<br>(pH: 7.4–8) | (0.5–3 ml)<br>Na pertechnetate<br>($^{99m}$Tc)<br>18 MBq to 3.7 GBq<br>(0.5–100 mCi) | 100° C., 30 min |
| 10 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>SnCl$_2$ ($1.7 \cdot 10^{-3}$<br>mole/l Na gluconate<br>(0.1 mole/l) | none | (0.5–3 ml)<br>Na pertechnetate<br>($^{99m}$Tc)<br>18 MBq to 3.7 GBq<br>(0.5–100 mCi) | 100° C., 30 min |
| 11 | (0.1–0.5 ml)<br>S-methyl, N-methyl<br>dithiocarbazate<br>($2 \cdot 10^{-2}$ mole/l<br>2.7 mg/ml | (0.1–0.2 ml)<br>SnCl$_2$ ($5.5 \cdot 10^{-4}$<br>mole/l) Na methylene<br>diphosphonate<br>($7 \cdot 10^{-3}$ mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | ambient temperature<br>30 min |
| 12 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>SnCl$_2$ ($7 \cdot 10^{-4}$<br>mole/l) Na hydroxymethylene<br>diphosphonate<br>($5 \cdot 10^{-3}$ mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | 100° C., 20 min |
| 13 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>SnCl$_2$ ($1 \cdot 10^{-3}$<br>mole/l Nacitrate<br>(0 1 mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | 100° C., 30 min |
| 14 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>Sn tartrate<br>($7 \cdot 10^{-4}$ mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | ambient temperature<br>30 min |
| 15 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>Sn tartrate<br>($7 \cdot 10^{-4}$ mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | 100° C., 30 min |
| 16 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>Sn oxalate<br>(saturated aqueous<br>solution) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | ambient temperature<br>30 min |
| 17 | (0.1–0.5 ml)<br>S-methyl, N-methyl<br>dithiocarbazate<br>($2 \cdot 10^{-2}$ mole/l<br>2.7 mg/ml | (0.1–0.5 ml)<br>Sn oxalate<br>(saturated aqueous<br>solution) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | 100° C., 20 min |
| 18 | (0.1–0.5 ml)<br>sodium nitride<br>($5 \cdot 10^{-2}$ mole/l) | (0.1–0.3 ml)<br>SnCl$_2$<br>($1.8 \cdot 10^{-3}$ mol<br>Na pyrophosphate<br>($5.6 \cdot 10^{-2}$ mole/l) | (1 ml)<br>phosphate buffer<br>(0.1–0 5 mole/l<br>pH: 7.4–8 | (0.5–3 ml)<br>Na pertechnetate<br>($^{99m}$Tc)<br>18 MBq to 3.7 GBq<br>(0.5–100 mCi) | 100° C., 30 min |
| 19 | (0.1–0.5 ml)<br>hydrazine dihydro-<br>chloride | (0.1–0.3 ml)<br>SnCl$_2$<br>($1.8 \cdot 10^{-3}$ mol | (0.1 ml)<br>1N HCl | (0.5–3 ml)<br>Na pertechnetate<br>($^{99m}$Tc) | 100° C., 30 min |

TABLE 1-continued

| Ex. | 1st nitrogen ligand | Reducing agent | Other additive | M oxygen compound | Reaction conditions |
|---|---|---|---|---|---|
|  | (0.1 mole/l) | Na pyrophosphate ($5.6 \cdot 10^{-2}$ mole/l) |  | 18 MBq to 3.7 GBq (0.5–100 mCi) |  |
| 20 | (0.1–0.5 ml) hydrazine dihydro-chloride (0.1 mole/l) | (0.1–0.3 ml) SnCl$_2$ $1.8 \cdot 10^{-3}$ mol Na pyrophosphate ($5.6 \cdot 10^{-2}$ mole/l) | (1 ml) PIPES buffer (piperazine diethane 1,4-sulphonic acid (0.1 mole/l pH: 5.0) | (0.5–3 ml) Na pertechnetate ($^{99m}$Tc) 18 MBq to 3.7 GBq (0.5–100 mCi) | 100° C., 30 min |
| 21 | (0.2 ml) acetohydrazide (0.13 mole/l) | (0.1–0.3 ml) SnCl$_2$ ($1.8 \cdot 10^{-3}$ mol) Na pyrophosphate ($5.6 \cdot 10^{-2}$ mole/l) | (1 ml) PIPES buffer (piperazine diethane 1,4-sulphonic acid (0.1 mole/l pH: 5.0) | (0.5–3 ml) Na pertechnetate ($^{99m}$Tc) 18 MBq to 3.7 GBq (0.5–100 mCi) | 100° C., 30 min |
| 22 | (0.2 ml) semicarbazide (0.1 mole/l) | (0.1–0.3 ml) SnCl$_2$ ($1.8 \cdot 10^{-3}$ mol) Na pyrophosphate ($5.6 \cdot 10^{-2}$ mole/l) | (1 ml) PIPES buffer (piperazine diethane 1,4-sulphonic acid (0.1 mole/l pH: 5.0) | (0.5–3 ml) Na pertechnetate ($^{99m}$Tc) 18 MBq to 3.7 GBq (0.5–100 mCi) | 100° C., 30 min |
| 23 | (0.4 ml) 2-methylthio semi carbazide ($5 \cdot 10^{-2}$ mole/l) | (0.1–0.3 ml) SnCl$_2$ ($1.8 \cdot 10^{-3}$ mol) Na pyrophosphate ($5.6 \cdot 10^{-2}$ mole/l) | (1 ml) PIPES buffer (piperazine diethane 1,4-sulphonic acid (0.1 mole/l pH: 5.0) | (0.5–3 ml) Na pertechnetate ($^{99m}$Tc) 18 MBq to 3.7 GBq (0.5–100 mCi) | 100° C., 30 min |
| 24 | (0.1–0.5 ml) S-methyl,N-methyl dithiocarbazate ($2 \cdot 10^{-2}$ mole/l) | (0.2 ml) Na dithionite ($6 \cdot 10^{-2}$ mole/l) | (1 ml) phosphate buffer (0.1–0.5 mole/l) pH: 7.4–8) | (0.5–3 ml) Na pertechnetate ($^{99m}$Tc) 18 MBq to 3.7 GBq (0.5–100 mCi) | 100° C., 30 min |

TABLE 2

| Ex. | Product | Second ligand | Tin complexing agent | Reaction conditions | Radiochemical purity |
|---|---|---|---|---|---|
| 25 | Ex. 1 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | 100° C., 15 min | >93% |
| 26 | Ex. 3 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | >98% |
| 27 | Ex. 4 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | >98% |
| 28 | Ex. 5 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | 100° C., 15 min | 96% |
| 29 | Ex. 6 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | 97% |
| 30 | Ex. 7 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | 95% |
| 31 | Ex. 8 | (0.5 ml) Na diethyldithio carbamate ($4 \cdot 10^{-2}$ mole/l) pH 7.5–11 | none | ambient temperature 15 min | 96% |
| 32 | Ex. 9 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | ≧97% |
| 33 | Ex. 10 | (0.5 ml) Na diethyldithio carbamate ($4 \cdot 10^{-2}$ mole/l) pH 7.5–11 | (0.2 ml) 1,2-N,N,N',N' diamino propane tetraacetic acid (0.33 mole/l) | ambient temperature 15 min | >92% |
| 34 | Ex. 11 | (0.5 ml) Na | (0.2 ml) | 100° C., 15 min | >94% |

TABLE 2-continued

| Ex. | Product | Second ligand | Tin complexing agent | Reaction conditions | Radiochemical purity |
|---|---|---|---|---|---|
| | | diethyldithio carbamate (4 · $10^{-2}$ mole/l) pH 7.5–11 | 1,2-N,N,N',N' diamino propane tetraacetic acid (0.33 mole/l) | | |
| 35 | Ex. 12 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | >92% |
| 36 | Ex. 13 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | >98% |
| 37 | Ex. 14 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | 100° C., 15 min | 95% |
| 38 | Ex. 15 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 98% |
| 39 | Ex. 16 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 98% |
| 40 | Ex. 18 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 95% |
| 41 | Ex. 19 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 93% |
| 42 | Ex. 20 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 92% |
| 43 | Ex. 21 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | 100° C., 15 min | 84% |
| 44 | Ex. 22 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | 100° C., 15 min | 88% |
| 45 | Ex. 23 | (0.5 ml) Na diethyldithio carbamate (4 · $10^{-2}$ mole/l) pH 7.5–11 | (0.2 ml) 1,2-N,N,N',N' diamino propane tetraacetic acid (0.33 mole/l) | ambient temperature 15 min | 97% |
| 46 | Ex. 24 | (0.5 ml) Na diethyldithio carbamate (4 · $10^{-2}$ mole/l) pH 7.5–11 | none | 100° C., 15 min | 91% |

TABLE 3

| Ex. | 1st nitrogen ligand | Reducing agent | Other additive | M oxygen compound | Reaction conditions |
|---|---|---|---|---|---|
| 47 | 1 ml tert.butyl carbazate (4 × $10^{-2}$ mole/l) 5.3 mg/ml $$\begin{array}{c}CH_3\\ \diagdown\\ \phantom{CH_3}CO-\overset{O}{\overset{\|}{C}}-NH-NH_2\\ \diagup\phantom{CH_3}|\\ CH_3\phantom{CO}CH_3\end{array}$$ | 0.5 ml $SnCl_2$, $2H_2O$ (9 × $10^{-4}$ mole/l) 1,2-N,N',N' diamino propane tetraacetic acid (6.5 × $10^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | 100° C. 30 min. |
| 48 | 1 ml benzyl hydrazine | 0.5 ml $SnCl_2$, $2H_2O$ | 1 ml | (0.5–3 ml) | 100° C. |

TABLE 3-continued

| Ex. | 1st nitrogen ligand | Reducing agent | Other additive | M oxygen compound | Reaction conditions |
|-----|---------------------|----------------|----------------|--------------------|---------------------|
|     | ($10^{-1}$ mol 13 6 mg/ml)<br>Ph—C(=O)—NH—NH$_2$ | ($9 \times 10^{-4}$ mole/l)<br>1,2-N,N,N',N'<br>diamino propane<br>tetraacetic acid<br>($6.5 \times 10^{-2}$ mole/l) | phosphate buffer<br>0.1–0.5 mole/l)<br>(pH = 7.4–8) | Na pertechnetate<br>($^{99m}$Tc)<br>18 MBq to 3,7 GBq<br>(0.5–100 mCi) | 30 min. |
| 49 | 0.2–0.5 ml<br>Girard reagent P<br>($2 \times 10^{-2}$ mol/l) 37 6 mg/ml<br>Py-N$^+$—CH$_2$—C(=O)—NH—NH$_2$, Cl$^\ominus$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 50 | 0.2–0 5 ml methyl<br>hydrazine carboxylate<br>($2 \times 10^{-2}$ mole/l) 18 mg/cc<br>CH$_3$—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 51 | 0.1–1 ml formyl hydrazine<br>($10^{-1}$ mole/l)<br>6 mg/ml<br>H—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 52 | 0.1–1 ml formyl hydrazine<br>($10^{-1}$ mole/l)<br>6 mg/ml<br>H—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 30 min.<br>ambient<br>temperature |
| 53 | 0.1–1 ml oxamyl hydrazine<br>($10^{-1}$ mole/l)<br>10 3 mg/ml<br>H$_2$N—C(=O)—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 54 | 0.1–1 ml cyanoaceto-<br>hydrazide ($10^{-1}$ mole/l)<br>9 9 mg/ml<br>N≡C—CH$_2$—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 55 | 0.1–1 ml syccinyl<br>dihydrazine ($10^{-1}$ mole/l)<br>14.6 mg/ml<br>H$_2$H—NH—C(=O)—CH$_2$CH$_2$—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | ambient<br>temperature<br>30 min. |
| 56 | 0.1–1 ml syccinyl<br>dihydrazine ($10^{-1}$ mol/l)<br>14.6 mg/ml<br>H$_2$H—NH—C(=O)—CH$_2$CH$_2$—C(=O)—NH—NH$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 57 | 0.1–1 ml 4-hydroxy<br>benzoyl hydrazide<br>($10^{-1}$ mole/l) 25.2 mg/ml<br>HO—C$_6$H$_4$—C(=O)—NH—HN$_2$ | 0.5 ml SnCl$_2$, 2H$_2$O<br>($9 \times 10^{-4}$ mole/l)<br>1,2-N,N,N',N'<br>diamino propane<br>tetraacetic acid<br>($6.5 \times 10^{-2}$ mole/l) | 1 ml<br>phosphate buffer<br>(0.1–0.5 mole/l)<br>(pH = 7.4–8) | (0.5–3 ml)<br>Na pertechnetate<br>($^{99m}$Tc)<br>18 MBq to 3,7 GBq<br>(0.5–100 mCi) | 100° C.<br>30 min. |
| 58 | 0.1–1 ml 4-aminobenzoyl<br>hydrazide ($10^{-1}$ mole/l)<br>15.1 mg/mol | 0.5 ml SnCl$_2$, 2H$_2$O<br>($9 \times 10^{-4}$ mole/l)<br>1,2-N,N,N',N' | 1 ml<br>phosphate buffer<br>(0.1–0.5 mole/l) | (0.5–3 ml)<br>Na pertechnetate<br>($^{99m}$Tc) | ambient<br>temperature<br>30 min |

TABLE 3-continued

| Ex. | 1st nitrogen ligand | Reducing agent | Other additive | M oxygen compound | Reaction conditions |
|---|---|---|---|---|---|
| | H$_2$N—C$_6$H$_4$—C(=O)—NH—NH$_2$ | diamino propane tetraacetic acid (6.5 × 10$^{-2}$ mole/l) | (pH = 7.4–8) | 18 MBq to 3,7 GBq (0.5–100 mCi) | |
| 59 | 0.1–1 ml 4-aminobenzoyl hydrazide (10$^{-1}$ mole/l) 15.1 mg/mol<br><br>H$_2$N—C$_6$H$_4$—C(=O)—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | 100° C. 30 min. |
| 60 | 0.1–1 ml meta-anisyl hydrazide (10$^{-1}$ mole/l) 16.6 mg/ml<br><br>(phenyl with OCH$_3$)—C(=O)—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | 100° C. 30 min. |
| 61 | 0.1–1 ml benzene (10$^{-1}$ mole/l) 17.2 mg/ml<br><br>C$_6$H$_5$—S(=O)$_2$—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | ambient temperature 30 min |
| 62 | 0.1–1 ml benzene (10$^{-1}$ mole/l) 17.2 mg/ml<br><br>C$_6$H$_5$—S(=O)$_2$—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | 100° C. 30 min. |
| 63 | 0.1–1 ml para-toluene sulphonyl hydrazide (10$^{-1}$ mole/l) 18.6 mg/ml<br><br>CH$_3$—C$_6$H$_4$—S(=O)$_2$—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | ambient temperature 30 min |
| 64 | 0.1–1 ml para-toluene sulphonyl hydrazide (10$^{-1}$ mole/l) 18.6 mg/ml<br><br>CH$_3$—C$_6$H$_4$—S(=O)$_2$—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | 100° C. 30 min. |
| 65 | 0.1–1 ml 2,4,5 trichlorobenzene sulphonyl hydrazide (10$^{-1}$ mole/l) 27.5 mg/ml<br><br>(2,4,5-Cl$_3$-C$_6$H$_2$)—S(=O)$_2$—NH—NH$_2$ | 0.5 ml SnCl$_2$, 2H$_2$O (9 × 10$^{-4}$ mole/l) 1,2-N,N,N',N' diamino propane tetraacetic acid (6.5 × 10$^{-2}$ mole/l) | 1 ml phosphate buffer (0.1–0.5 mole/l) (pH = 7.4–8) | (0.5–3 ml) Na pertechnetate ($^{99m}$Tc) 18 MBq to 3,7 GBq (0.5–100 mCi) | ambient temperature 30 min |
| 66 | 0.1–1 ml 2,4,5 trichlorobenzene sulphonyl hydrazide (10$^{-1}$ mole/l) 27.5 mg/ml | 0.5 ml SnCl$_2$, 2H$_2$O (9 × 10$^{-4}$ mole/l) 1,2-N,N,N',N' diamino propane | 1 ml phosphate buffer (0.1–0.5 mole/l) (pH = 7.4–8) | (0.5–3 ml) Na pertechnetate ($^{99m}$Tc) 18 MBq to 3,7 GBq | 100° C. 30 min. |

TABLE 3-continued

| Ex. | 1st nitrogen ligand | Reducing agent | Other additive | M oxygen compound | Reaction conditions |
|---|---|---|---|---|---|
|  | 2,4,6-trichlorobenzene sulphonyl hydrazide (Cl, Cl, Cl substituents on benzene ring with $-S(=O)_2-NH-NH_2$) | | tetraacetic acid ($6.5 \times 10^{-2}$ mole/l) | (0.5–100 mCi) | |
| 67 | 0.1–1 ml 2,4,6 trimethyl benzene sulphonyl hydrazide ($10^{-1}$ mole/l) 21.4 mg/ml (CH$_3$, CH$_3$, CH$_3$ substituents on benzene ring with $-S(=O)_2-NH-NH_2$) | 0.5 ml SnCl$_2$, 2H$_2$O ($9 \times 10^{-4}$ mole/l) | 1 ml phosphate buffer (0.1–0.5 mole/l) (pH = 7.4–8) 1,2-N,N,N',N' diamino propane tetraacetic acid ($6.5 \times 10^{-2}$ mole/l) | (0.5–3 ml) Na pertechnetate ($^{99m}$Tc) 18 MBq to 3,7 GBq (0.5–100 mCi) | ambient temperature 30 min. |
| 68 | 0.1–1 ml 2,4,6 trimethyl benzene sulphonyl hydrazide ($10^{-1}$ mole/l) 21.4 mg/ml (CH$_3$, CH$_3$, CH$_3$ substituents on benzene ring with $-S(=O)_2-NH-NH_2$) | 0.5 ml SnCl$_2$, 2H$_2$O ($9 \times 10^{-4}$ mole/l) | 1 ml phosphate buffer (0.1–0.5 mole/l) (pH = 7.4–8) 1,2-N,N,N',N' diamino propane tetraacetic acid ($6.5 \times 10^{-2}$ mole/l) | (0.5–3 ml) Na pertechnetate ($^{99m}$Tc) 18 MBq to 3,7 GBq (0.5–100 mCi) | 100° C. 30 min. |
| 69 | 0.1 ml of S-methyl, N-methyl dithiocarbazate (0.2 mg/ml) | 0.2 ml SnCl$_2$, 2H$_2$O ($4 \cdot 10^{-3}$ mole/l) | 1 ml phosphate buffer (0.1–0.5 mole/l) (pH = 7.4–8) sodium 1,2-diamino-N,N,N',N'-propane tetraacetate (0.16 mole/l) | (0.5–3 ml) Na pertechnetate ($^{99m}$Tc) 18 MBq to 3,7 GBq (0.5–100 mCi) | ambient temperature 30 min. |

TABLE 4

| Ex. | Product | Second ligand | Reaction conditions | Radiochemical purity |
|---|---|---|---|---|
| 70 | Ex. 47 | 0.5 ml Na diethyl dithiocarbamate ($4 \times 10^{-2}$ mol/l) pH = 7.5–11 | 15 min. | 96% |
| 71 | Ex. 48 | 0.5 ml Na diethyl dithiocarbamate ($4 \times 10^{-2}$ mol/l) pH = 7.5–11 | " | 94% |
| 72 | Ex. 49 | 0.5 ml Na diethyl dithiocarbamate ($4 \times 10^{-2}$ mol/l) pH = 7.5–11 | " | 98% |
| 73 | Ex. 50 | 0.5 ml Na diethyl dithiocarbamate ($4 \times 10^{-2}$ mol/l) pH = 7.5–11 | " | 98% |
| 74 | Ex. 51 | 0.5 ml Na diethyl dithiocarbamate ($4 \times 10^{-2}$ mol/l) pH = 7.5–11 | " | 90% |
| 75 | Ex. 52 | 0.5 ml Na diethyl dithiocarbamate ($4 \times 10^{-2}$ mol/l) pH = 7.5–11 | " | 96% |
| 76 | Ex. 53 | 0.5 ml Na diethyl dithiocarbamate ($4 \times 10^{-2}$ mol/l) pH = 7.5–11 | " | 95% |
| 77 | Ex. 54 | 0.5 ml Na diethyl dithiocarbamate ($4 \times 10^{-2}$ mol/l) pH = 7.5–11 | " | 90% |
| 78 | Ex. 55 | 0.5 ml Na diethyl dithiocarbamate ($4 \times 10^{-2}$ mol/l) pH = 7.5–11 | " | 98% |
| 79 | Ex. 56 | 0.5 ml Na diethyl dithiocarbamate ($4 \times 10^{-2}$ mol/l) pH = 7.5–11 | " | 96% |
| 80 | Ex. 57 | 0.5 ml Na diethyl dithiocarbamate ($4 \times 10^{-2}$ mol/l) pH = 7.5–11 | " | 94% |
| 81 | Ex. 58 | 0.5 ml Na diethyl dithiocarbamate ($4 \times 10^{-2}$ mol/l) pH = 7.5–11 | " | 90% |
| 82 | Ex. 59 | 0.5 ml Na diethyl dithiocarbamate ($4 \times 10^{-2}$ mol/l) pH = 7.5–11 | 15 min. | 85% |
| 83 | Ex. 60 | 0.5 ml Na diethyl dithiocarbamate ($4 \times 10^{-2}$ mol/l) pH = 7.5–11 | " | 90% |
| 84 | Ex. 61 | 0.5 ml Na diethyl dithiocarbamate ($4 \times 10^{-2}$ mol/l) pH = 7.5–11 | " | 92% |

TABLE 4-continued

| Ex. | Product | Second ligand | Reaction conditions | Radiochemical purity |
|---|---|---|---|---|
| 85 | Ex. 62 | 0.5 ml Na diethyl dithiocarbamate $(4 \times 10^{-2}\,mol/l)$ pH = 7.5–11 | " | 96% |
| 86 | Ex. 63 | 0.5 ml Na diethyl dithiocarbamate $(4 \times 10^{-2}\,mol/l)$ pH = 7.5–11 | " | 91% |
| 87 | Ex. 64 | 0.5 ml Na diethyl dithiocarbamate $(4 \times 10^{-2}\,mol/l)$ pH = 7.5–11 | " | 96% |
| 88 | Ex. 65 | 0.5 ml Na diethyl dithiocarbamate $(4 \times 10^{-2}\,mol/l)$ pH = 7.5–11 | " | 96% |
| 89 | Ex. 66 | 0.5 ml Na diethyl dithiocarbamate $(4 \times 10^{-2}\,mol/l)$ pH = 7.5–11 | " | 97% |
| 90 | Ex. 67 | 0.5 ml Na diethyl dithiocarbamate $(4 \times 10^{-2}\,mol/l)$ pH = 7.5–11 | " | 91% |
| 91 | Ex. 68 | 0.5 ml Na diethyl dithiocarbamate $(4 \times 10^{-2}\,mol/l)$ pH = 7.5–11 | " | 96% |
| 92 | Ex. 69 | 0.5 ml Na diethyl dithiocarbamate $(4 \times 10^{-2}\,mol/l)$ pH = 7.5–11 | " | 96% |
| 93 | Ex. 8 | 1 ml 2-thioquinoline 1 mg/ml pH = 7.80 | 100° C. 30 min. | >90% |
| 94 | " | 1 ml (D.L) penicillamine 10 mg/ml pH = 7.80<br>$(CH_3)_2C-CHCOOH$ with SH and $NH_2$ substituents | Ambient temperature 30 min. | 95% |
| 95 | " | 1 ml sodium ethyl dithiocarboxylate 10 mg/ml pH = 3.5<br>$CH_3-CH_2-C(=S)(S^\ominus Na^\oplus)$ | Ambient temperature 30 min. | 85% |
| 96 | " | 1 ml sodium isopropyl xanthate 10 mg/ml pH = 7.80<br>$(CH_3)_2CH-O-C(=S)(S^\ominus Na^\oplus)$ | Ambient temperature 30 min. | >90% |
| 97 | Ex. 8 | 1 ml sodium diethyl dithiophosphinate 10 mg/ml pH = 5<br>$Et_2P(=S)(S^\ominus Na^\oplus)$ | Ambient temperature 30 min. | >90% |

We claim:

1. Process for the preparation of a product incorpoting a nitride complex of a transition metal having a part M≡N with M representing the transition metal, comprising the step of reacting a solution of an oxygen compound of the transition metal M with:

1°) a first nitrogen ligand comprising a pharmaceutically acceptable metal or ammonium nitride, or a nitrogen compound having a

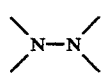

unit, in which the N's are connected to hydrogen atoms and/or monovalent organic groups or in which one of the N's is connected to the carbon atom of a divalent organic group by means of a double bond and the other N is connected to hydrogen atoms and/or monovalent organic groups and 2°) a reducing agent comprising a pharmaceutically acceptable metal or ammonium dithionite, or tin (II) present in ionic form in the solution wherein said transition metal is Tc or Re.

2. Process for the preparation of a product incorporating a nitride complex of a transition metal having a part M≡N, in which M represents the transition metal, comprising the step of reacting a solution of an oxygen compound of the transition metal M with:

1°) a first nitrogen ligand comprising a pharmaceutically acceptable metal or ammonium nitride, or a nitrogen compound having a

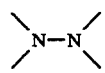

unit, in which the N's are connected to hydrogen atoms and/or to monovalent organic groups, or in which one of the N's is connected to the carbon atom of a divalent organic group by means of a double bond and the other N is connected to hydrogen atoms and/or to monovalent organic groups, 2°) a reducing agent comprising a pharmaceutically acceptable metal or ammonium dithionite, or by tin (II) present in ionic form in the solution and 3°) a second organic ligand having a member selected from the group consisting of a nucleophilic group, a monoclonal antibody, an antibody fragment, a protein and a peptide wherein said transition metal is Tc or Re.

3. Process according to claim 2, characterized in that, in a first stage, the oxygen compound of the transition metal is reacted with the first ligand and the reducing agent, and in a second stage, the product obtained at the end of the first stage is reacted with the second ligand, the monoclonal antibody or the antibody fragment.

4. Process according to claim 2, characterized in that simultaneous reaction takes place between the oxygen compound of the transition metal and the first nitrogen ligand, the reducing agent and the second ligand or the monoclonal antibody or antibody fragment.

5. Process according to any one of the claims 1 to 4, characterized in that the reducing agent is tin (II) and in that it is introduced in ionic form into the solution by adding a tin (II) salt and a complexing agent to a solution of the transition metal oxygen compound and the first nitrogen ligand.

6. Process according to claim 5, characterized in that the tin (II) salt is tin (II) chloride.

7. Process according to any one of the claims 1 to 3, characterized in that the reducing agent is tin (II) and in that it is introduced into the solution in the form of a tin (II) salt.

8. Process according to claim 7, characterized in that the tin (II) salt is tin (II) oxalate or tartrate.

9. Process according to any one of the claims 1 to 3, characterized in that the reducing agent is sodium dithionite.

10. Process according to any one of the claims 1 to 4, characterized in that the solution is an aqueous solution.

11. Process according to claim 10, characterized in that the aqueous solution has a pH of 7 to 8.

12. Process according to any one of the claims 1 to 4, characterized in that the first nitrogen ligand is S-methyl, N-methyl dithiocarbazate.

13. Process according to any one of the claims 1 to 4, characterized in that the first nitrogen ligand is chosen from the group consisting of sodium nitride, hydrazine, acetohydrazide, semicarbazide and 2-methyl thiosemicarbazide.

14. Process according to any one of the claims 1 to 4, characterized in that the first nitrogen ligand is in accordance with the formula:

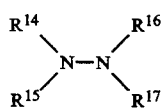

in which $R^{14}$, $R^{15}$ and $R^{16}$, which can be the same or different, represent a hydrogen atom, an alkyl radical, an aryl radical, an alkoxy radical, an alkyl radical substituted by at least one group chosen from the group consisting of hydroxy, carboxy, amino, amido and mercapto radicals or an aryl radical substituted by at least one group chosen from the group consisting of halogen atoms and alkoxy, hydroxy, amino and mercapto radicals and amino radicals substituted by at least one alkyl radical, $R^{17}$ represents a radical complying with the formulas $$-SO_2R^{18}$$

or $$-CO\ R^{19}$$

in which $R^{18}$ is a phenyl group, which is not substituted or substituted by at least one substituent chosen from the group consisting of the halogen atoms and the alkyl radicals and $R^{19}$ is a hydrogen atom, $-NH_2$ or a radical chosen from the group consisting of alkyl radicals, alkyl radicals substituted by at least one group chosen from the group consisting of cyano, pyridyl and $-CO-NH-NH_2$ groups, the phenyl radical, the phenyl radical substituted by at least one substituent chosen from the group consisting of $-OH$, $NH_2$ and alkyl and alkoxy radicals.

15. Process according to claim 14, characterized in that $R^{14}$, $R^{15}$ and $R^{16}$ are hydrogen atoms, $R^{17}$ represents the radical of formula $SO_2R^{18}$ with $R^{18}$ having the meaning given in claim 14, or the radical of formula COH, $CO-CH_2-CH_2-CO-NH-NH_2$ or

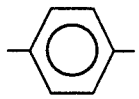

$NH_2$, and in that the reaction is performed at ambient temperature.

16. Process according to claim 15, characterized in that $R^{17}$ represents $SO_2R^{18}$ with $R^{18}$ being the phenyl radical, the p-methyl phenyl radical, the 1,3,5-trichlorophenyl radical or the 1,3,5-trimethyl phenyl radical.

17. Process according to any one of the claims 2 to 4, characterized in that the second ligand is sodium diethyl dithiocarbamate.

18. Process according to any one of the claims 2 to 4, characterized in that the second ligand is chosen from the group consisting of thioquinoline, penicillamine, sodium ethyl dithiocarboxylate, sodium isopropyl xanthate and sodium diethyl dithiophosphonate.

19. Process according to any one of the claims 1 to 4, characterized in that the transition metal oxygen compound is an ammonium or alkali metal pertechnetate −99 m.

20. Process according to any one of the claims 1 to 4, characterized in that the transition metal oxygen compound is ammonium or alkali metal perrhenate −186 or −188.

21. Kit for the preparation of a transition metal nitride complex by performing the process according to any one of the claims 2 to 4, characterized in that it incorporates a first bottle containing the first nitrogen ligand and the reducing agent and a second bottle containing a second organic ligand with a nucleophilic group, a monoclonal antibody, an antibody fragment, a protein or a peptide.

22. Process according to claim 5, characterized in that the complexing agent is chosen from the group consisting of ammonium of alkali metal pyrophosphates, ammonium or alkali metal glucoheptonates, ammonium or alkali metal diethylene triaminopentaacetates, ammonium or alkali metal ethylene diaminotetraacetates, ammonium or alkali metal 1,2-diamino-N,N,N',N'-propane tetraacetates, ammonium or alkali metal gluconates, ammonium or alkali metal methylene diphosphonates, ammonium or alkali metal hydroxymethylene diphosphonates and ammonium or alkali metal citrates.

23. Process according to claim 6, characterized in that the complexing agent is chosen from the group consisting of ammonium of alkali metal pyrophosphates, ammonium or alkali metal glucoheptonates, ammonium or alkali metal diethylene triaminopentaacetates, ammonium or alkali metal ethylene diaminotetraacetates, ammonium or alkali metal 1,2-diamino-N,N,N',N'-propane tetraacetates, ammonium or alkali metal gluconates, ammonium or alkali metal methylene diphosphonates, ammonium or alkali metal hydroxymethylene diphosphonates and ammonium or alkali metal citrates.

* * * * *